United States Patent [19] [11] Patent Number: 4,936,851
Fox et al. [45] Date of Patent: Jun. 26, 1990

[54] ANALYTIC BONE IMPLANT

[75] Inventors: William C. Fox; William T. Balogh; Phontie J. Pantermuehl; Thomas B. Aufdemorte; George R. Holt, all of San Antonio, Tex.

[73] Assignee: Colin Electronics Co., Ltd., Komaki, Japan

[21] Appl. No.: 236,865

[22] Filed: Aug. 26, 1988

[51] Int. Cl.⁵ .............................................. A61F 2/28
[52] U.S. Cl. ..................................................... 623/16
[58] Field of Search ........................... 623/16, 18, 1, 66

[56] References Cited
FOREIGN PATENT DOCUMENTS
0269175 6/1988 European Pat. Off. .............. 623/16
0269176 6/1988 European Pat. Off. .............. 623/16

Primary Examiner—Richard J. Apley
Assistant Examiner—David Isabella
Attorney, Agent, or Firm—Matthews & Branscomb

[57] ABSTRACT

A analytic bone implant includes a cylindrical housing with an inner chamber designed for collecting sample of bone tissues. The outer surface of the housing is provided with a plurality of threads for securing the implant into bone tissue. The housing is further provided with a plurality of openings to allow new bone tissue to grow into a collecting basket. The openings in the housing are alignable with complementary openings in the basket. The openings on the basket are provided with sharp edges which serve as cutting blades to facilitate the removal of the bone sample. The implant includes provision for repeated access to the medullary compartment for obtaining sample of cancellous tissue for histologic and morphometric analysis.

8 Claims, 15 Drawing Sheets

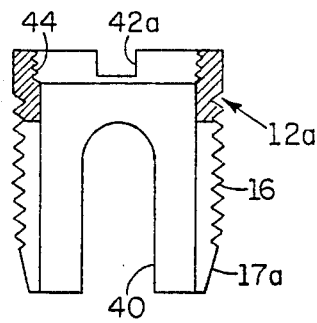 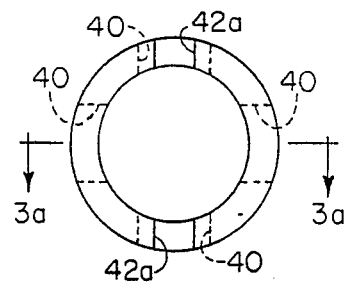
FIG. 3a　　　　　FIG. 3b
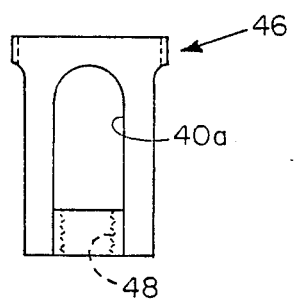 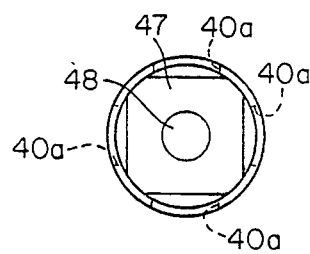
FIG. 4a　　　　　FIG. 4b

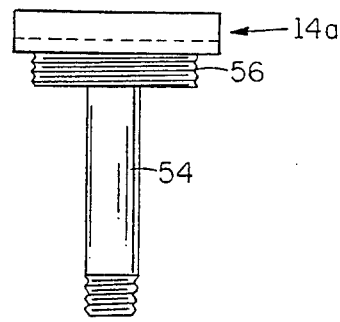
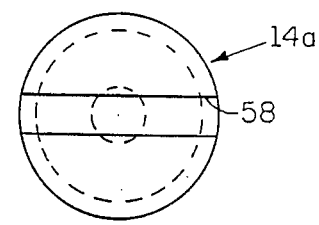
FIG. 5a    FIG. 5b
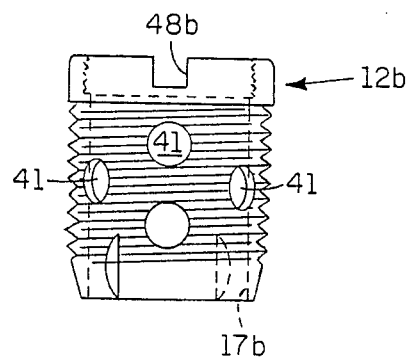
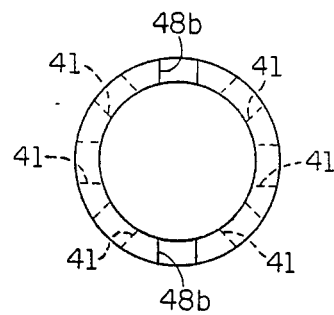
FIG. 6a    FIG. 6b

ANALYTIC BONE IMPLANT

FIELD OF THE INVENTION

The present invention relates generally to the field of in-vivo implants for biomedical applications. More specifically, the present invention provides a means for obtaining permanent atraumatic access to otherwise inaccessible biological tissues which are protected or covered by hardened bone structures. This invention allows cancellous bone and marrow as well as organs surrounded by hardened cortical bone to be accessed repeatably from the same site with minimal surgical trauma and morbidity.

BACKGROUND

In the field of bone and mineral research, it is important to be able to access metabolic tissue for the purpose of diagnosis or determining the pathogenesis of disease and efficacy of treatment. Access to osseous tissue is complicated by traumatic surgical intervention. Therefore, previously available data from hard tissue samples has been susceptible to wide variance due to the adverse impacts of surgical procedures and sampling instrumentation.

An effective bone sampling instrument must be capable of removing a sample without undue alteration of the morphology of the tissue. Further, the apparatus must be biocompatible, evoking no foreign body responses while it is implanted in the bone tissue. In addition, bone-implant interference and chemical adhesions must be of such a nature that the apparatus becomes a permanent fixture in the bone.

The required level of fixation or integration has been demonstrated with materials such as commercially pure titanium, titanium alloys, and titanium coatings. Titanium has the advantages of high strength, light weight, machinability and biocompatible corrosion behavior. U.S. Pat. No. 4,330,891 issued to Branemark is directed to a method for forming a titanium oxide material which is inert when placed in bone. Prior investigations both in the United States and abroad indicate that implants of titanium in bone become osseointegrated within weeks or months. Titanium and titanium alloys have been used for constructing oral prostheses, cardiac pacemaker housings, and fasteners for reconstructive surgery.

To date, there has been no teaching in the prior art of an effective apparatus for removing a sample of living bone tissue without undue destruction of the bone morphology. The analytic bone implant device of the present invention, as described in greater detail hereinbelow, overcomes the difficulties related to prior bone sampling techniques by providing a means for a permanent atraumatic access to otherwise inaccessible biological tissues. Tissues of interest include cancellous bone and marrow, cells, and physiologic fluids.

SUMMARY OF THE INVENTION

The Analytic Bone Implant (ABI) of the present invention provides a means for obtaining a significant sample of cancellous tissue for histologic and morphometric analysis. This bone implant device provides samples of cancellous bone and access to the medullary space. The provision for repeated accesses to the medullary compartment of bone is a significant and unique feature of the ABI.

Briefly, the Analytic Bone Implant of the present invention comprises a generally cylindrical housing having a predetermined length and an inner chamber for collecting the sample of bone tissue. The outer surface of the housing is provided with a plurality of threads for securing the ABI into bone tissue. The housing is further provided with a plurality of openings to allow bone tissue to grow into a collecting means in the interior of the housing for subsequent removal. In the preferred embodiment of the ABI, the access ports comprise arched slots in the housing which are alignable with complementary arched slots in a basket assembly. The arched slots on the basket assembly are provided with sharp edges which serve as cutting blades to facilitate the removal of the bone sample. In an alternate embodiment, the access ports are a plurality of generally circular apertures in a spaced geometric pattern in the housing.

In the preferred embodiment, the collection means is in the form of a generally cylindrical basket assembly which is received in the interior of the housing. In the alternate embodiment of the invention, the collection means is a "cup" assembly which is defined by a disk having a diameter approximately the same as the interior of the implant housing. The disk is secured in the housing by a shaft which is attached to the cap of the implant. When the cap of the implant is removed, the disk is pulled though the housing to force the tissue sample out of the inner chamber of the housing.

The various embodiments of the Analytic Bone Implant of the present invention provide at least ten novel features and advantages over the sampling devices of the prior art. First, access trauma is minimized because the cap of the chamber can be accessed by a small surgical incision. Second, bone access ports allow communication between the core of the device and the medullary space for the transmission of mechanical stresses and physiologic substances. Third, chamber volume can be varied to optimize bone growth. Fourth, the housing protects the bone sample and facilitates bone removal. Fifth, the inner volume provides a large sample for histomorphometric studies and could accommodate small devices or drug deliver systems. Sixth, bone marrow access is provided once the cap and the core are removed. Seventh, sampling is facilitated by a cutting blade which engages during cap removal shearing the bone at the internal aspect of the access ports. Eighth, small size which allows implantation in a variety of species and sites. Ninth, biocompatibility which is achieved by the use of titanium or titanium alloy with a clean and sterile surface. Tenth, tissue may be obtained for in vitro studies, including isolation of bone cell populations and osteotropic factors.

BRIEF DESCRIPTION OF THE DRAWINGS

FIG. 3a is a cross-sectional side view of the housing of preferred embodiment of the analytic bone implant showing the geometric placement of the bone access slots.

FIG. 3b is a top view of the housing of the preferred embodiment showing the placement of the insertion slots therein.

FIG. 4a is an elevational side view of the tissue sampling basket with cutters of the preferred embodiment of the analytic bone implant.

FIG. 4b is a top view of the tissue sampling basket of the preferred embodiment of the analytic bone implant.

FIG. 5a is an elevational side view of the cap with mandrel of the analytic bone implant.

FIG. 5b is an elevational top view of the cap with mandrel of the analytic bone implant.

FIG. 6a is a elevational side view of the alternate embodiment of analytic bone implant housing showing details relating to the placement of bone access ports therein.

FIG. 6b is a top view of the alternate embodiment of analytic bone implant housing showing the geometric placement of the bone access ports and insertion slots.

DETAILED DESCRIPTION OF THE PREFERRED EMBODIMENT

Figure 1:
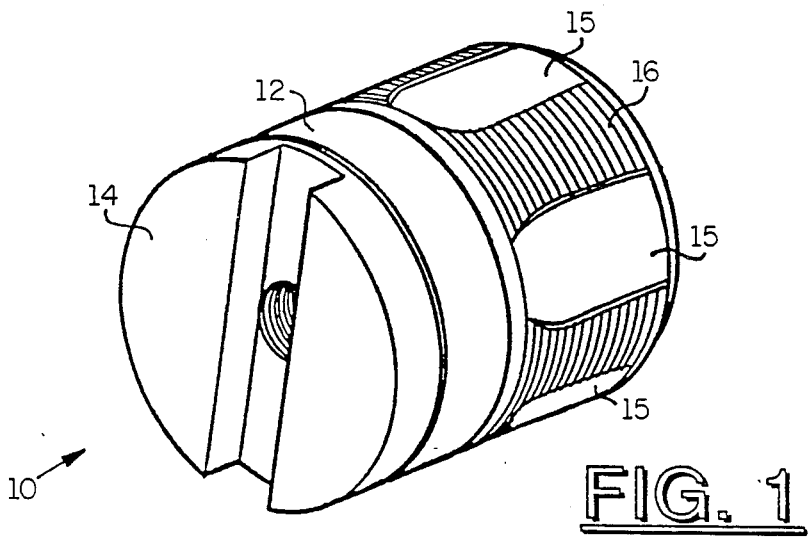
FIG. 1 is an elevated perspective view of the analytic bone implant of the present invention.

Referring to the drawings in more detail, and to the elevational perspective view of FIG. 1 in particular, a conceptual illustration of the Analytic Bone Implant 10 (hereinafter sometimes called "ABI") of the present invention is shown. The implant is broadly comprised of a housing 12, a cap assembly 14, and a removable insert assembly (sample collecting means), described in greater detail below. The housing serves as a mount and achieves this function through osseointegration or fixation in the surrounding bone tissue. Specifically, the housing 12 is formed of an appropriate titanium alloy, discussed below, that has biocompatiblity properties which facilitate the growth of bone tissues into the threads 16 in the outer surface of the housing 12. The housing 12 is provided with a plurality of access ports, illustrated generally by reference number 15, which provide a path for growth of bone tissue into the collecting means in the interior of the housing.

Figure 2:
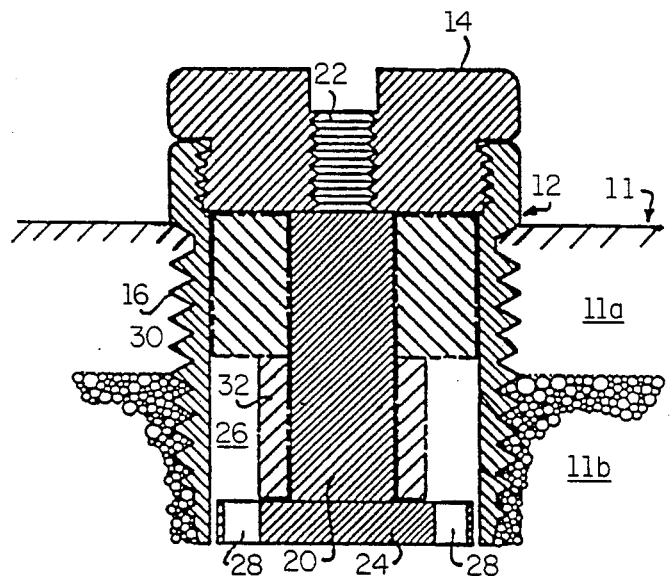
FIG. 2 is a cross-sectional view of the analytic bone implant of the present invention in-situ in a portion of bone tissue.

Referring to the cross-sectional view of FIG. 2, a conceptual view is shown of the ABI embedded in a portion of bone 11. The ABI is positioned in the bone such that the access cap 14 is external to the bone and the periosteum, but below the epidermis. The threads 16 of the housing 12 are tightly held in the surrounding bone tissue. In the position shown in FIG. 2, the upper threads of the housing are embedded in cortical bone 11a, while the lower threads are embedded in medullary tissue 11b. The ABI has a length of approximately eight millimeters and a diameter of approximately eight millimeters.

The cross-sectional side view of FIG. 2 depicts a generalized conceptual embodiment of the ABI insert assembly and is shown for the purposes of illustration only. However, this figure shows many of the features of the alternate embodiment of the present invention and thus it will be described briefly to aid in the understanding of the invention. Briefly, the collecting means of this embodiment is an insert assembly which includes a vertical shaft 20 having a threaded portion 22 which is received in a threaded central bore 22 in the cap 14 of the ABI. The lower end of the shaft 20 is attached to a disk 24 having an outer diameter approximately equal to the inner diameter of the housing 12. Bone tissue grows into the inner chamber 26 of the ABI via a plurality of openings 15 in the housing 12. In addition, in the embodiment of the ABI shown in FIG. 2, bone tissue enters the chamber 26 also via a plurality of apertures 28 in the lower disk 24. The volume of the chamber 26 can be varied by inserting various combinations of collars into the inner chamber 26, for example, the collars 30 and 32 shown in FIG. 2.

In order to understand the advantages offered by the present invention, it is important to have a general understanding of bone growth kinetics. When the ABI inserted into a site in the patient's bone, an "injury" condition is created. The injury created by the insertion of the implant is similar to that of an uncomplicated fracture site. Healing of the site is a continuous process involving three phases: (1) organization of thrombus; (2) procallous to callous or fibrocartilage formation; and (3) formation of osseous callous and remodeling. There are concurrent histologic, ultrastructural, systemic responses and biochemical events at the healing site. The bone that ultimately forms in the ABI chamber is identical to that which results from stimulation of osseogenesis under a variety of conditions in humans. Qualitative and quantitative data on the status of the bone-healing process can be acquired by analyzing samples from the ABI chamber. Once new bone is sampled from the chamber, a fresh endosseous wound (fracture) site is created and the healing process is restarted.

Details relating to the housing of the preferred embodiment of the ABI can be seen by referring to FIGS. 3a and 3b. In the embodiment shown in FIG. 3a, the housing 12a comprises a plurality of arch-like slots 40 which provide a path for bone growth into a sampling chamber on the interior of the housing 12a. Each of the slots 40 is provided with a cutting edge which aids in the removal of an undamaged sample of bone tissue. Referring to FIG. 3b, it can be seen that the preferred embodiment of the housing contains a total of four arch-like slots 40, although the exact number of slots can be varied depending on the specific application of the implant. The four slots of the preferred embodiment are placed at 90 degree intervals around the perimeter of the housing.

The outer surface of the housing 12a is provided with a plurality of threads 16, FIG. 3a, for securing the housing in bone tissue. The lower edge 17a of the housing is tapered and the lower threads are tapered also to provide a means for self-tapping insertion of the ABI housing into the sampling site. The upper portion of the housing is provided with a slot 42a for receiving an insertion tool which is used to rotate the housing to cause the threads to engage the bone tissue. To place the ABI into the bone it is necessary to first create a bore having a coarsely threaded inner surface. This can be accomplished through the use of any number of commonly available medical threading devices which are well known in the art. Once this coarsely threaded bore has been established, the ABI housing can be threaded into the bore by inserting an appropriate tool into the slot 42a in the upper portion of the housing and turning the housing to cause the threads 16 on the outer surface to engage the coarse threads on the inner surface of the insertion site. After the housing has been threaded into the bore, bone tissue will migrate into the threads 16 to secure the housing more firmly.

A tissue sampling basket 46 of the preferred embodiment is illustrated in FIGS. 4a and 4b. The outer diameter of the sampling basket is chosen to allow the basket to be received within the housing 12a, FIG. 3a. As can be seen in FIG. 4a, the basket 46 is provided with a plurality of arch-like slots 40a which are alignable with the slots 40 in the housing 12a of FIG. 3a. Furthermore, each of the slots 40a is provided with cutting edges which cooperate with the edges of the slots 40 in the housing 12a to cut the sample of bone tissue when the sampling basket is removed from the housing. The lower portion of the basket 46 is provided with a plate 47, FIG. 4b, having a threaded aperture 48 which is adapted to receive complimentary threads 52 on the lower end of the shaft 54 of a cap 14a, shown in FIG. 5a.

Referring now to FIGS. 5a and 5b, the cap 14a also has a threaded portion 56 which is engagable with threads 44 in the inner surface of the housing 12a, shown in FIG. 3a, to secure the cap and basket assembly within the housing. The threads of the aperture 52 and the threads 56 on the cap 14a have opposite inclines so that the basket 46, FIG. 4a, is turned by the cap 14a to perform the cutting off of the bone sample when the cap is removed from the housing.

Details relating to a housing 12b of an alternate embodiment of the ABI can be seen by referring to FIGS. 6a and 6b. The housing 12b has many of the features discussed above in connection with the housing of the preferred embodiment. However, bone access in the alternate embodiment is provided by a plurality of apertures 41 which are in a spaced geometric pattern in the housing. In the alternate embodiment of the ABI a total of twelve apertures are used to provide a path for bone migration into the inner chamber of the housing. The upper portion of the housing 12b is provided with a slot 48b which is adapted to receive an appropriate tool, as discussed above in connection with the preferred embodiment.

Figure 7A:
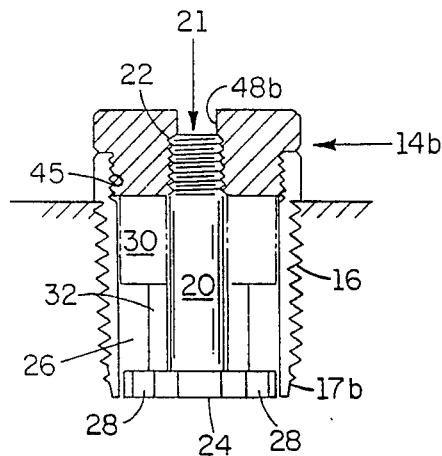
FIG. 7a is an cross-sectional side view of the cap of the alternate embodiment of analytic bone implant housing.
Figure 7B:
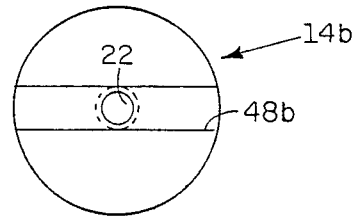
FIG. 7b is a top view of the cap of the alternate embodiment of analytic bone implant housing.
Figure 7C:
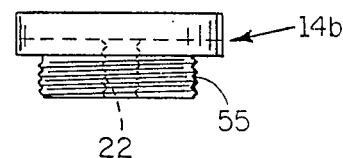
FIG. 7c is a side view of the cap of the alternate embodiment of the analytic bone implant housing.
Figure 8A:
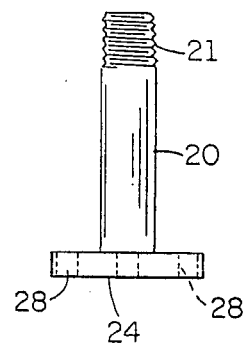
FIG. 8a is an elevational side view of the alternate embodiment of tissue sampling cup of the analytic bone implant.
Figure 8B:
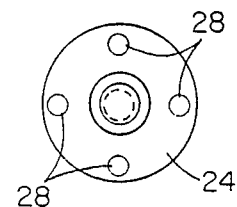
FIG. 8b is an top view of the alternate embodiment of tissue sampling cup of the analytic bone implant.

FIG. 7a is a cross-sectional view of the assembled ABI of the alternate embodiment. As discussed above, the collecting means of this embodiment is an insert assembly which includes a vertical shaft 20 having a threaded portion 21 which is received in a threaded central bore 22 in a cap 14b. The lower end of the shaft 20 is attached to a disk 24 having an outer diameter approximately equal to the inner diameter of the housing 12b, FIG. 6a. Bone tissue grows into the inner chamber 26 of the ABI via the plurality of apertures 41 in the housing 12b. In addition, bone tissue enters the chamber 26 via a plurality of apertures 28 in the lower disk 24, also seen in FIG. 8b. The volume of the chamber 26 can be varied by inserting various combinations of collars into the inner chamber 26, for example, the collars 30 and 32 shown in FIG. 7a.

The housings of both embodiments are designed with sufficient surface area to promote tissue-device adhesion while allowing bone, cells, vessels and other tissues to enter the devices' core through apertures or slots in the housing. The cap serves several purposes: (1) access to the core of the device, (2) fixation mount for core assembly, and (3) prevention of connective tissue encroachment into the ABI chamber. In all applications, the insert allows removal of tissues from the ABI chamber.

Once the bone has grown into the ABI chamber, removal of the cap facilitates sample removal. In the preferred embodiment of the ABI, the act of unscrewing and removing the cap will shear the tissue entering the chamber through the entry ports providing a structurally intact sample of consistent volume. When the insert-cap assembly is disassembled, a cylinder of bone with a hole down its longitudinal axis can be removed. The tissue sample obtained from the preferred embodiment of the ABI is approximately 0.01 cubic inches.

Although the Analytic Bone Implant of the present invention has been described in connection with its preferred embodiment, it is not intended to be limited to the specific forms set forth herein, but, on the contrary, it is intended to cover such modifications, alternatives and equivalents as can reasonably be included within the scope and spirit of the invention as defined by the appended claims.

We claim:

1. An analytic bone implant for repeated acquisition of substantially undeformed osseous tissue from a site in a bone, comprising:

a housing having a generally cylindrical outer surface, an inner chamber, and a predetermined length terminating in two ends;

said inner chamber having a generally smooth wall extending from one of said two end to the other;

said outer surface having threads, for engaging cortical or medullary tissue in said bone, said threads beginning a predetermined distance from one of said two ends and extending to the other of said two ends, and having a predetermined number of openings to permit bone growth into said inner chamber;

cutting means substantially contiguous with said bone growth openings for separating new bone growth said cutting means cooperating with said closure cap to cut said new bone growth upon removal of said cap; and basket means to collect said new bone growth after separation by said cutting means.

2. An analytic bone implant as described in claim 1, wherein said means to collect said new bone growth includes disc means supported from said closure cap means beneath said openings to collect said new bone growth.

3. An analytic bone implant as described in claim 2, including insert means attached to said closure cap means, extending therefrom, and attached to said disc means to support said disc means from said closure cap means.

4. An analytic bone implant as described in claim 3 wherein said outer surface of said housing includes at least two openings positioned diametrically opposite each other to permit bone-growth into the inner chamber.

5. The analytic bone implant as described in claim 4, said access ports comprising arched slots in said housing, said slots being alignable with complementary arch slots in said basket assembly.

6. An analytic bone implant as described in claim 5, said arch slots on said basket assembly being provided with sharp edges for cutting said new bone growth.

7. An analytic bone implant as described in claim 6, said housing and said basket each comprising a total of four arch slots.

8. An analytic bone implant for repeated acquisition of substantially undeformed osseous tissue from a site in a bone, comprising:

a housing having a generally cylindrical outer surface, an inner chamber, and a predetermined length terminating in two ends, said housing having a tapered portion of one end thereof;

said inner chamber having a generally smooth wall extending from one of said two ends to the other;

said outer surface having threads on said tapered portion of said housing, for engaging cortical or medullary tissue in said bone, said threads beginning a predetermined distance from one of said two ends and extending to the other of said two ends, and having a predetermined number of openings to permit bone growth into said inner chamber;

closure cap means threaded onto said housing at said one end;

cutting means substantially contiguous with said bone growth openings for separating new bone growth said cutting means cooperating with said closure cap to cut said new bone growth upon removal of said cap; and basket means to collect said new bone growth after separation by said cutting means.

* * * * *